(12) United States Patent
Hörnig

(10) Patent No.: US 8,009,798 B2
(45) Date of Patent: Aug. 30, 2011

(54) X-RAY IMAGING SYSTEM

(75) Inventor: Mathias Hörnig, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 78 days.

(21) Appl. No.: 12/522,316

(22) PCT Filed: Jan. 21, 2008

(86) PCT No.: PCT/EP2008/050626
§ 371 (c)(1),
(2), (4) Date: Jul. 7, 2009

(87) PCT Pub. No.: WO2008/090118
PCT Pub. Date: Jul. 31, 2008

(65) Prior Publication Data
US 2009/0296881 A1    Dec. 3, 2009

(30) Foreign Application Priority Data
Jan. 23, 2007 (DE) .......................... 10 2007 003 380

(51) Int. Cl.
*A61B 6/04* (2006.01)
*H05G 1/02* (2006.01)

(52) U.S. Cl. ......................................... 378/37; 378/196

(58) Field of Classification Search .................... 378/37, 378/62, 193, 195–197, 204–206
See application file for complete search history.

(56) References Cited

U.S. PATENT DOCUMENTS

| 4,613,982 A * | 9/1986 | Dornheim et al. ............. 378/37 |
| 5,386,447 A | 1/1995 | Siczek |
| 5,598,269 A * | 1/1997 | Kitaevich et al. ............. 356/399 |
| 6,292,531 B1 | 9/2001 | Hsieh |
| 6,999,554 B2 * | 2/2006 | Mertelmeier ................... 378/37 |
| 2004/0109529 A1 | 6/2004 | Eberhard et al. |
| 2005/0008124 A1 * | 1/2005 | Ullberg ......................... 378/197 |
| 2005/0129172 A1 * | 6/2005 | Mertelmeier ................... 378/37 |
| 2006/0291618 A1 | 12/2006 | Eberhard et al. |
| 2008/0165933 A1 | 7/2008 | Hornig |

FOREIGN PATENT DOCUMENTS

| DE | 103 19 305 A1 | 11/2004 |
| DE | 10 2004 034 241 | 2/2006 |
| WO | WO 98/49939 | 11/1998 |
| WO | WO 2006/061357 | 6/2006 |

* cited by examiner

*Primary Examiner* — Anastasia Midkiff
(74) *Attorney, Agent, or Firm* — Schiff Hardin LLP

(57) ABSTRACT

In a method and an apparatus for medical imaging, the radiation source is aligned relative to a detector plate, and the alignment is controlled so that the high-energy being emitted the radiation source always strikes the detector plate with a symmetrical distribution relative to a central ray of the radiation source.

6 Claims, 3 Drawing Sheets

X-RAY IMAGING SYSTEM

BACKGROUND OF THE INVENTION

1. Field of the Invention

The invention concerns a device and an associated method for a medical diagnosis with a high-energy radiation source. High-energy photons are emitted by this high-energy radiation source and detected by a high-energy detector associated with the high-energy radiation source. A subject to be examined is arranged between the high-energy radiation source and the high-energy detector.

2. Description of the Prior Art

Devices and methods of the above type are generally known in the field of mammography for the examination of the breast. Mammography is in particular used for early detection of breast cancer. For this purpose, the breast to be examined is compressed between a compression plate and a detector plate and is irradiated with x-rays that are generated by an x-ray source. A fixing and/or an alignment or, respectively, arrangement of the subject to be examined on the detector plate or detector unit ensues by a displacement of the compression plate.

A deflection of the x-ray beam through an automatic tracking of the diaphragms arranged at the x-ray aperture of the x-ray source ensues, that is coupled with the displacement of the compression plate. This deflection of the x-ray beam entails the disadvantage that—due to the deflection of central x-ray beam—a reduced irradiation and thus reduced resolution occurs in tissue parts that are situated in border regions of the detector. The reduced resolution leads to a reduced image quality.

SUMMARY OF THE INVENTION

An object of the invention is to provide a diagnosis system of the aforementioned type achieves with an optimal image quality.

In the device according to the invention and the associated method a radiation source is aligned in relation to border regions of the detector unit such that the high-energy rays of the radiation source always strike the detector unit with a symmetrical distribution relative to a central ray of the x-ray source.

The invention has the advantage that individual conditions and requirements in the examination of the breast can be accommodated.

The invention also has the advantage that an optimal use of the radiation emitted by the high-energy radiation source can be achieved.

The invention also has the advantage that, in addition to selectable compression plates with specific device angulations, an optimal use of the radiation emitted by the high-power source can be achieved in connection with a coordination between the central, symmetrical alignment of x-ray beam relative to the detector.

The invention also has the advantage that all regions of the subject to be considered can be shown in an image for a diagnosis.

The invention also has the advantage that a consistent, optimized image quality is ensured even in border regions.

In an embodiment, an exact positioning of the radiation source can be conducted via sensors.

In an embodiment, the diagnosis unit can automatically be driven into a centered default position via a reset button.

In a further embodiment the radiation source can be aligned via an activation of a light field on the subject.

In another embodiment an optimized gain correction can be employed.

In addition to the advantage of an easy operation via a slider button, the invention has the additional advantage that a workflow is improved through this function.

The invention has the advantage that image processing operations for rectifying resolution losses, image sharpness or intensity decrease at the edge of a subject to be examined are not needed.

DESCRIPTION OF THE PREFERRED EMBODIMENTS

Figure 1:
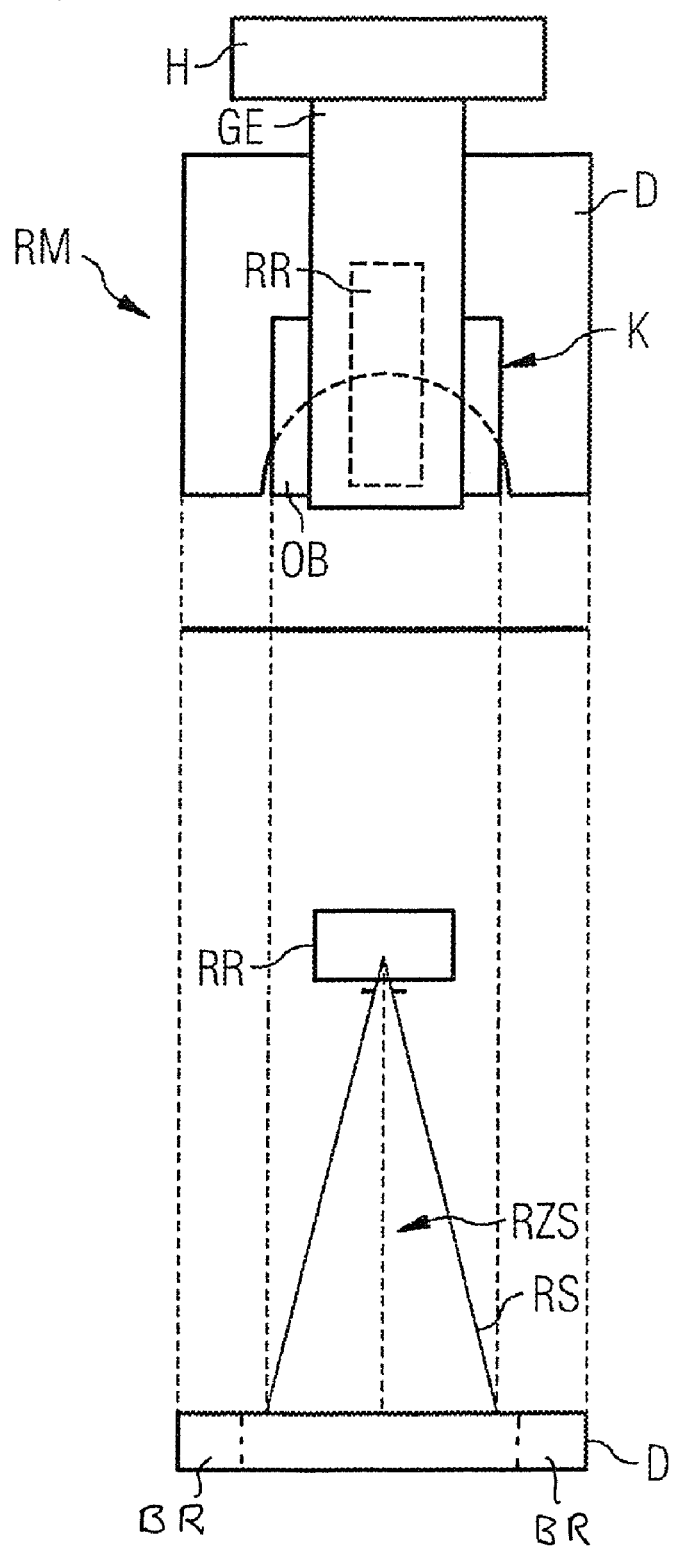
FIG. 1 shows a schematic plan view (upper portion) and a schematic front view (lower portion) of a first embodiment of a mammography apparatus constructed and operating in accordance with the present invention.

A plan view of a schematic representation of a mammography apparatus RM is shown in the upper part of FIG. 1.

The housing unit ge arranged on a mount H has an x-ray source RR emitting x-ray radiation. The mammography apparatus RM also comprises a detector unit or, respectively, detection plate D possessing flat panel detectors, as well as a compression plate K. A mamma OB (also called a subject in the following, can be aligned or, respectively, fixed between detection plate D and compression plate K.

Figure 2:
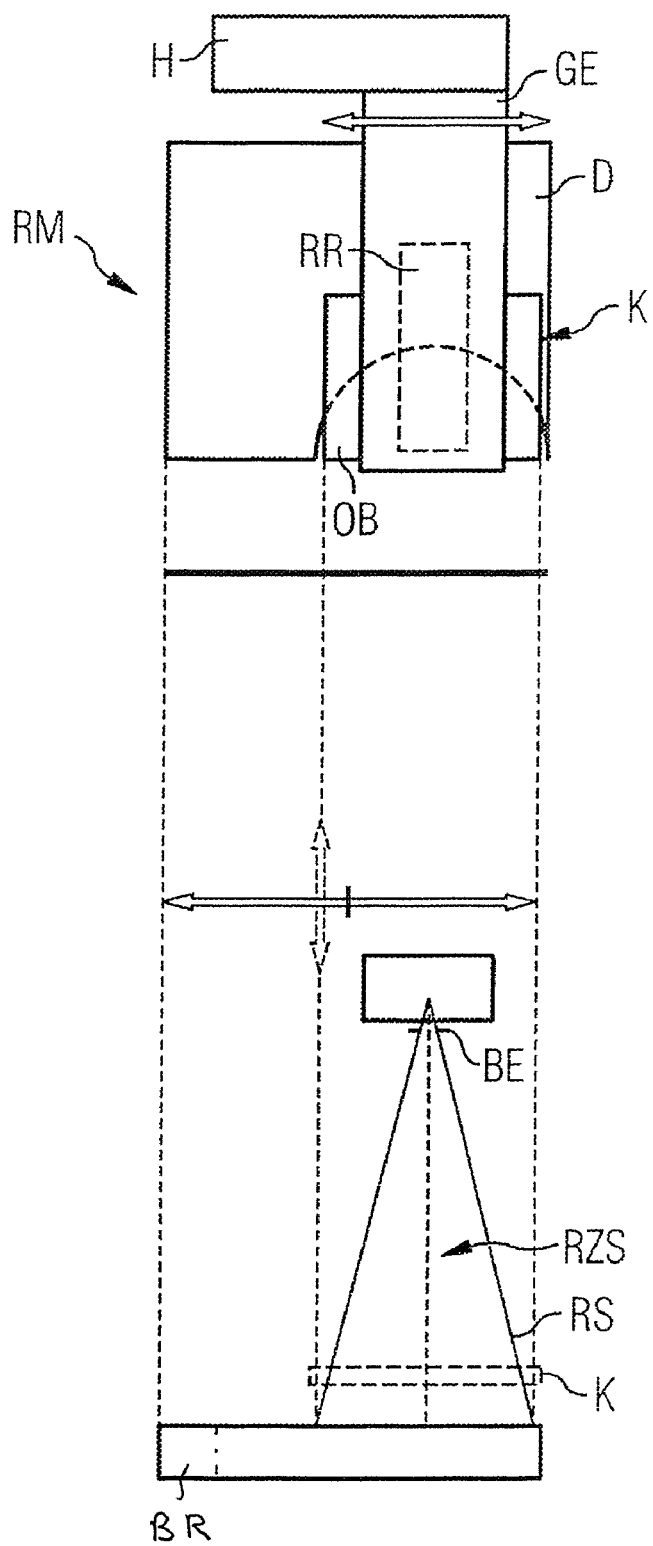
FIG. 2 shows a schematic plan view (upper portion) and a schematic front view (lower portion) of a second embodiment of a mammography apparatus constructed and operating in accordance with the present invention.

The front view of the schematic representation of the mammography apparatus RM is shown in the lower part of FIG. 1. The radiation region of the x-rays RS emitted by the x-ray tube RR as well as the course of the central x-ray RZS are shown. The region in which the x-ray RS strikes the detector plate D is likewise indicated. The detector plate D has border regions BR (shown at the sides in the front view in FIG. 1 and at the front in the side view of FIG. 2) that lie outside the region struck by the x-rays RS Another embodiment of a mammography apparatus RM according to the invention is shown in FIG. 2. In the plan view in the upper part of FIG. 2, the x-ray tube RR and the compression plate D are viewed as a unit. A collimator for filtering the x-ray radiation RS can be associated with this unit. A housing unit GE incorporating the x-ray tube RR is connected with the mount H such that it can be fixed. This housing unit GE can be horizontally displaced. A vertical shift of the housing unit GE can likewise be conducted.

A front view of the mammography apparatus RM is shown in the lower part of FIG. 2. The unit can be displaced corresponding to the indicated movement directions such that a position in which each region of the mamma that is to be examined can be reached with an undeflected x-ray beam can be adopted for the time period of the examination of the patient.

By the use of differing sizes of compression plates at specific device angulations, the embodiment enables an improved patient access. The device angulation can be implemented with a C-arm typical to diagnostic apparatuses, for example. The local alignment of the housing unit GE accommodating the x-ray tube ensues by means of electrical actuating means, for example. The position of the unit can be shifted either continuously or to positioning points by means of a shift button. A fixing of the housing unit GE in connection with the compression unit ensues via releasing the slider button. A fixing can also ensue in the manner of a grid, wherein the position can also be acoustically indicated. An automatic activation of a light field can ensue at the collimator simultaneously with the shifting of the unit E, such that a visual presentation of the selected examination region or, respectively, image region is immediately provided.

Figure 3:
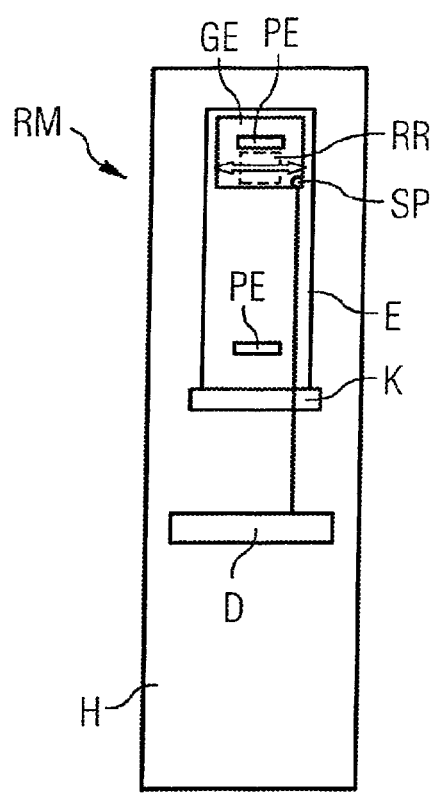
FIG. 3 is a schematic front view of an embodiment of a mammography apparatus in accordance with the present invention, in a first operating state.
Figure 4:
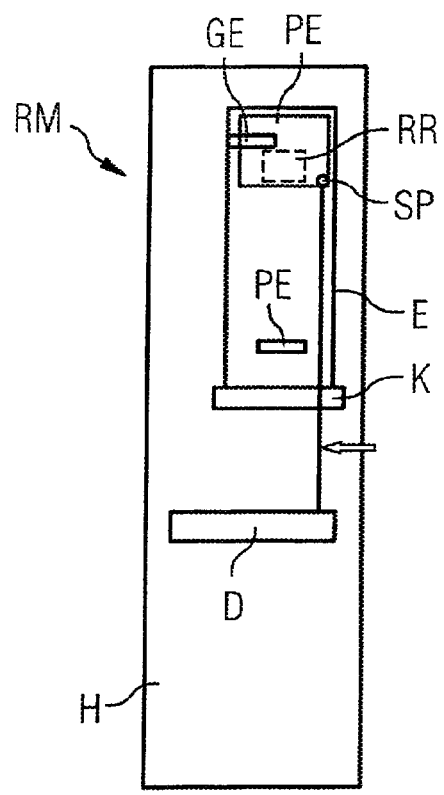
FIG. 4 is a schematic front view of an embodiment of a mammography apparatus in accordance with the present invention, in a second operating state.

An embodiment of a mammography apparatus RM with the unit E (already desorbed) is schematically shown in a front view in FIGS. 3 and 4. This unit E consists of, among other things, the housing unit GE, the x-ray source RR integrated into the housing unit and the compression plate K. The position elements PE bounding the deflection of the unit E are drawn in, for example. FIG. 3 shows the mammography apparatus RM with the unit E in a starting or rest position. The unit E is displaced to the right in FIG. 4. A positioning of the unit E can ensue via a stepper SP arranged in the housing GE. This can exactly determine the positioning of the x-ray tube RR or, respectively, that of x-ray radiation emanating from this to the detector D. A fine control of the unit E in or out of an operating position can thereby be conducted with the assistance of laser technology or via reflection measurement. An alignment can likewise ensue by means of memory function. A mechanically implementable positioning is also possible in addition to the electrical and electronic positioning.

A calibration can be conducted at least in the central, left-of-center and right-of-center positions. A linear interpolation by means of a gain mapping is additionally possible for possible intermediate positions.

In an alternative embodiment the slider function ensues continuously, limited only by a left-side and right-side end position. The left-side and right-side end position can be predetermined by the border region of the x-ray beam at the detector edge. The position detection can ensue by means of laser technology. A central position of the x-ray tube can be taken up again via a reset function. The position of the unit E can be stored by the operating system of the diagnostic unit and be retrieved for new examinations.

In an additional embodiment, the information from a positioning can be used in order to focus on a preselected detector region and to save time for the data read out, data transfer and data processing.

In an additional embodiment, tube and diaphragm unit are shifted synchronously. The operating system of the diagnostic unit RM has an automatic position detection and a reset function with which the tube and diaphragm unit BE, including the compression plate K, can be respectively driven into the central starting position. The focusing by means of the stepper SP can ensue either via laser diode or via reflection measurement, or mechanically by means of a memory function.

Although modifications and changes may be suggested by those skilled in the art, it is the intention of the inventor to embody within the patent warranted heron all changes and modifications as reasonably and properly come within the scope of his contribution to the art.

I claim as my invention:

1. An x-ray imaging apparatus comprising:
   a unitary component comprising a radiation source that emits high-energy radiation in a radiation pattern having a central ray, and a compression plate in an unchanging position relationship with respect to said radiation source;
   a radiation detector unit;
   said radiation source and said radiation detector unit being configured to receive an examination subject therebetween and said compression plate being configured to compress the examination subject between the compression plate and the detector, and said radiation detector unit being configured to detect said high-energy radiation emitted by said radiation source, attenuated by said examination subject compressed by said compression plate, said radiation detector unit comprising a border region; and
   a supporting unit to which said unitary component and said radiation detector unit are mounted, said supporting unit being configured to move said unitary component relative to said radiation to align the examination subject between the radiation source and the radiation detector unit, by always maintaining a symmetrical distribution, relative to the central ray of said radiation pattern, of said high-energy radiation striking said radiation detector unit.

2. A device as claimed in claim 1 wherein said supporting unit is configured to horizontally and vertically modify the position of the unitary component, to place the radiation source in a modified position, and to fix the unitary component to also fix the radiation source in said modified position.

3. A device as claimed in claim 1 wherein said supporting unit is configured to position the unitary component dependent on said border region of said radiation detector unit.

4. A method for operating an x-ray imaging apparatus comprising the steps of:
   irradiating an examination subject with high-energy radiation emitted by a radiation source, said high energy radiation having a radiation pattern with a central ray;
   detecting said high-energy radiation emitted by said radiation source, attenuated by said examination subject, with a radiation detector unit comprising a border region, while compressing the examination subject against the radiation detector unit with a compression plate; and
   maintaining the radiation source and the compression plate in an unchanging position relationship in a unitary component, and mounting said unitary component and said radiation detector unit on a supporting unit and moving said unitary component on supporting unit to position said radiation source to align an examination subject between the radiation source and the radiation detector unit, by always maintaining a symmetrical distribution, relative to the central ray of said radiation source, of said high-energy radiation striking said radiation detector unit.

5. A method as claimed in claim 4 comprising moving said unitary component to horizontally and vertically modify the position of the unitary component, to place the radiation source in a modified position, and fixing the unitary component in said modified position.

6. A method as claimed in claim 4 comprising adjusting said unitary component to position the radiation source dependent on said border region of said radiation detector unit.

* * * * *